(12) United States Patent
Gottenbos et al.

(10) Patent No.: US 11,185,400 B2
(45) Date of Patent: Nov. 30, 2021

(54) ADMINISTRATION OF ORAL CARE AGENTS

(71) Applicant: KONINKLIJKE PHILIPS N.V., Eindhoven (NL)

(72) Inventors: Bart Gottenbos, Budel (NL); Carl Glasse, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 219 days.

(21) Appl. No.: 16/305,962

(22) PCT Filed: May 30, 2017

(86) PCT No.: PCT/EP2017/062977
§ 371 (c)(1),
(2) Date: Nov. 30, 2018

(87) PCT Pub. No.: WO2017/207533
PCT Pub. Date: Dec. 7, 2017

(65) Prior Publication Data
US 2019/0216585 A1 Jul. 18, 2019

(30) Foreign Application Priority Data
Jun. 3, 2016 (EP) .................................... 16172830

(51) Int. Cl.
*A61C 19/06* (2006.01)
*A61C 15/00* (2006.01)
(Continued)

(52) U.S. Cl.
CPC ............ *A61C 19/063* (2013.01); *A61C 15/00* (2013.01); *A61K 9/0063* (2013.01); *A61K 9/06* (2013.01);
(Continued)

(58) Field of Classification Search
CPC ...... A61C 15/00; A61C 19/063; A61K 47/12; A61K 47/26; A61K 47/36
(Continued)

(56) References Cited

U.S. PATENT DOCUMENTS 4,983,379 A * 1/1991 Schaeffer ............... A61K 8/042
424/52
8,747,899 B2 6/2014 Chaput et al.
(Continued)

FOREIGN PATENT DOCUMENTS

EP 0202359 A2 * 11/1986 ............... A61K 8/19
EP 0202359 A2 11/1986
(Continued)

OTHER PUBLICATIONS

Bisht et al: "In-Situ-Gel: A Study of Dental Diseases"; Indian Journal of Novel Drug Delivery 6 (3), Jul.-Sep. 2014, pp. 208-214.
(Continued)

*Primary Examiner* — Matthew M Nelson (57) ABSTRACT

Disclosed is a method, and a system, for accomplishing the in situ formation of a gel in an interdental space. This is useful for the interdental application of one or more dental care agents, such as antimicrobial agents or other anti-plaque agents. The invention makes use of a two component system comprising a gelable liquid and a liquid gelling agent capable of bringing about gelation of the liquid. The system of the invention is arranged such that first the gelable, typically viscous, liquid can be applied, and then the liquid gelling agent is forced, e.g. jetted, into the applied gelable liquid. The system is designed such as to prevent the gelling agent and the gelable liquid to come into contact with each other before both have been applied. The system is configured to allow the gelable liquid to be applied prior to the gelling agent.

7 Claims, 2 Drawing Sheets

(51) Int. Cl.
  *A61K 9/00* (2006.01)
  *A61K 9/06* (2006.01)
  *A61K 47/12* (2006.01)
  *A61K 47/26* (2006.01)
  *A61K 47/36* (2006.01)

(52) U.S. Cl.
  CPC .............. *A61K 47/12* (2013.01); *A61K 47/26* (2013.01); *A61K 47/36* (2013.01)

(58) Field of Classification Search
  USPC .......................................................... 433/80
  See application file for complete search history.

(56) References Cited

U.S. PATENT DOCUMENTS

| | | | |
|---|---|---|---|
| 2007/0292367 A1* | 12/2007 | Clarot | A61J 7/04 424/52 |
| 2008/0255498 A1* | 10/2008 | Houle | A61C 17/0211 604/20 |
| 2010/0221196 A1* | 9/2010 | Gottenbos | A61Q 11/00 424/49 |
| 2014/0227657 A1* | 8/2014 | Sanders | A61C 5/90 433/32 |
| 2014/0308625 A1* | 10/2014 | Fairley | A61C 17/028 433/88 |
| 2016/0113640 A1 | 4/2016 | Soma | |
| 2017/0079755 A1* | 3/2017 | Kovacevic-Milivojevic | A61C 17/028 |
| 2019/0216585 A1* | 7/2019 | Gottenbos | A61K 47/12 |

FOREIGN PATENT DOCUMENTS

| | | |
|---|---|---|
| EP | 2296637 B1 | 4/2014 |
| KR | 20060059403 | 6/2006 |
| WO | 2007066837 A1 | 6/2007 |
| WO | 2008135957 A2 | 11/2008 |
| WO | 2016050573 A1 | 4/2016 |
| WO | 2016097927 A1 | 6/2016 |
| WO | 2017089394 A1 | 6/2017 |

OTHER PUBLICATIONS

Madan et al: "In Situ Forming Polymeric Drug Delivery Systems"; Indian Journal of Pharmaceutical Sciences, May-Jun. 2009, vol. 7 (13), pp. 242-251.

\* cited by examiner

ADMINISTRATION OF ORAL CARE AGENTS

CROSS-REFERENCE TO PRIOR APPLICATIONS

This application is the U.S. National Phase application under 35 U.S.C. § 371 of International Application No. PCT/EP2017/062977, filed on May 30, 2017, which claims the benefit of European Patent Application No. 16172830.8, filed on Jun. 3, 2016. These applications are hereby incorporated by reference herein.

FIELD OF THE INVENTION

The invention is in the field of oral care, and pertains to a method and a device for the deposition, into the oral cavity, of oral care agents via a composition formed in situ. Particularly, the invention pertains to the interdental administration of antimicrobial agents, notably antiplaque agents.

BACKGROUND OF THE INVENTION

Dental plaque is a biofilm or mass of bacteria that grows on surfaces within the mouth. It is commonly found between the teeth and along the cervical margins. Dental plaque is also known as microbial plaque, oral biofilm, dental biofilm, dental plaque biofilm or bacterial plaque biofilm. While plaque is commonly associated with oral diseases such as caries and periodontal diseases (gum diseases), its formation is a normal process that cannot be prevented.

Dental plaque can give rise to dental caries (tooth decay)—the localised destruction of the tissues of the tooth by acid produced from the bacterial degradation of fermentable sugar—and periodontal problems such as gingivitis and periodontitis. Its progression and build up is what leads to oral problems, hence it is important to disrupt the mass of bacteria and remove it daily.

It is customary to control and remove plaque by means of tooth brushing and interdental aids such as dental floss or oral irrigators.

Removal of dental biofilm is important as it may become acidic causing demineralisation of the teeth (also known as caries) or harden into calculus (also known as tartar). Calculus cannot be removed through toothbrushing or with interdental aids and can only be removed through professional cleaning. Therefore, removal of the dental biofilm will prevent the development of caries and gum diseases.

A persistent problem is that removal of dental plaque is hardly ever complete, and that quick regrowth is difficult to prevent. To this end, antimicrobial agents are widely used for the control of dental plaque in for example mouthrinses and toothpastes. They are capable of inactivating dental plaque biofilms that are left over after mechanical toothbrushing or flossing. After application however, the concentrations of these agents tends to drop quickly due to saliva flow, eating and drinking. Therefore the agents cannot prevent recolonization of the teeth with new bacteria and dental plaque can regrow quickly, to adversely affect the health of teeth and gums.

In order to prevent such recolonization with new bacteria, more of the antimicrobial agent should be maintained on and/or around the tooth surface. This cannot be well achieved by merely increasing the concentration of the agents, as the concentration as such does not lead to a longer residence time, or even may lead to toxic concentrations of the agents. Rather, the problem to be addressed is that of providing a better substantivity of the antimicrobial agents, i.e., a longer residence time in the oral cavity. Hitherto this has been a challenge to the skilled person.

In the art, a recent technology is based on compositions such as gels or varnishes to be applied on teeth. One such method is disclosed in WO 2008/135957. This concerns a method for cleaning dental plaque biofilm from teeth wherein a liquid gelable composition is applied to the teeth. From the composition a gel layer is produced, wherein the gel layer adheres more strongly to the dental plaque biofilm than the biofilm adheres to the teeth. Ultimately the gel layer is removed from the teeth, and the dental plaque biofilm along therewith, as the dental plaque biofilm adheres to the gel layer. The in situ formation of the gel can be realized by first administering a gelable liquid (e.g. based on chitosan), and then administering a second liquid as a gelling agent (e.g. a sodium hydroxide solution) to bring about gelation.

SUMMARY OF THE INVENTION

The method disclosed in WO 2008/135957 is particularly directed to applying a gel layer over the surface of teeth. The method thereby disclosed still requires improvement as to the quality of the gel to be formed. For, if the crosslinking solution (the liquid gelling agent) is simply placed on top of the gelable liquid, or is applied as a rinse, only the outside layer of the polymer solution is crosslinked. This results in a film of hydrogel, with fluidic polymer solution still within. Such a film is prone to relatively easy rupture, after which the active agents applied via the gelable composition would be lost from the mouth.

Further, a problem to be addressed, is that of providing a suitable composition for the delivery of oral care agents into interdental spaces. Particularly, a challenge thereby is provide adequate substantivity of the oral care agents in such interdental spaces. Considering the saliva environment of the mouth, agents will be readily washed away from the interdental spaces, if not contained in a suitable structure such as an adhesive gel. However, to apply a gel to interdental spaces is difficult. The gel layer of WO 2008/135957, which is directed at providing a peelable structure applied over teeth, does not sufficiently reach the interdental spaces.

In accordance with the invention, it is particularly desired to provide a method of achieving in situ gel formation also in interdental spaces. This gel should serve to apply oral care agents to interdental spaces. This is useful for agents such as antimicrobials, but also for any other type of oral care agent for which interdental delivery would be desired.

However, the interdental space can be up to 10 mm long. As a result diffusion of the cross-linker molecules would take much too long (e.g. more than 15 minutes), to be able to bring about gel formation over the entire interdental space.

The invention as defined by the independent claims aims to better address the foregoing desires.

In one aspect the invention provides a delivery system for the application into an interdental space of a gelable liquid and a liquid gelling agent, at least one of the gelable liquid and the liquid gelling agent comprising an oral care agent, wherein the delivery system comprises:
 a first container holding the gelable liquid and an aperture configured to exit the gelable liquid into an interdental space, the container being in fluid communication with the aperture, and
 a second container holding the liquid gelling agent, and a nozzle configured to exit the gelling agent into the interdental space, the second container being in fluid communication with the nozzle, and wherein the system is configured to, during use, allow the gelable liquid to exit the aperture prior to allowing the liquid gelling agent to exit the nozzle, and to prevent the gelling agent and the gelable liquid to contact each other before exiting the delivery system.

The invention thus provides a delivery system for the application into an interdental space of a gelable liquid comprising an oral care agent and a liquid gelling agent for said gelable liquid, wherein the system comprises a first container configured to hold the gelable liquid, said first container being in fluid communication with an aperture configured to exit the gelable liquid into an interdental space, and a second container configured to hold the liquid gelling agent, said second container being in fluid communication with a nozzle configured to exit the gelling agent into an interdental space, wherein the system is designed such as to prevent the gelling agent and the gelable liquid to come into contact with each other before both have been exited, and wherein the system is configured to allow the gelable liquid to be exited prior to the gelling agent.

The respective containers of the delivery system may actually hold the gelleable liquid and the liquid gelling agent.

According to another aspect of the invention there is provided a kit of parts for use in applying a gel comprising an oral care agent into an interdental space of a subject, the kit of parts including a first part and a second part, the first part including a gelable liquid and the second part including a liquid gelling agent capable of causing gelation of the gellable liquid when it contacts the gellable liquid, at least one of the gelable liquid and the liquid gelling agent comprising an oral care agent and wherein the gel is obtained by applying the gelable liquid into the interdental space and, subsequently, applying the gelling agent into the applied gelable liquid.

In another aspect, the invention provides a method for applying a gel comprising an oral care agent into an interdental space of a subject, the method comprising the steps of:
  applying a gelable liquid into the interdental space, and, subsequently,
  applying a liquid gelling agent into the applied gelable liquid, the liquid gelling agent capable of causing gelation of the gelable liquid when brought in contact with the gellable liquid,
  wherein at least one of the gelable liquid and the liquid gelling agent comprises an oral care agent.

The invention in all its aspects, delivery system, kit of parts (also referred to as a two-component composition) and method is thus directed towards the in situ formation of said gel in said interdental space. This formation of the gel is improved with regard to the known methods by first applying the gelable liquid into the interdental space, and, subsequently, applying the gelling agent into (as distinguished from onto). the applied gelable liquid. In this way intimate mixing contact between the gelable liquid and the liquid gelling agent is achieved such that diffusion time of the gelling agent is reduced and the gel can be formed in the deeper parts of interdental space at reduced time.

The dependent claims provide advantageous embodiments.

In one important embodiment, the invention presents a delivery system, kit of parts or method for the treatment or prevention of dental plaque in a subject, where the gel comprises an oral care agent in the form of a anti plaque agent.

DETAILED DESCRIPTION OF THE EMBODIMENTS

In a general sense, the invention relates to any ensemble of components and a method of application of such components to form a composition suitable for the in situ formation of an interdental gel. The ensemble preferably is in the form of a kit of parts. One of the parts including a first component and a second part including a second component. Such components generally are a gelable liquid and a corresponding gelling agent (which can also be referred to as a gelation agent) which is capable of inducing gelation of the gelable liquid when brought in contact with the gellable liquid. The invention is based on the judicious insight that the in situ formation of such interdental gel can be accomplished by first applying the gelable liquid into an interdental space, and then applying the gelling agent into (and not merely onto) the gelable liquid as present in said interdental space. An oral care agent preferably is included in the gelable liquid.

The terms "interdental" and "interdental space" refer to the space, or gap, between teeth. In the art this is generally also referred to as "interproximal" and "interproximal space."

The gelable liquid and the liquid gelling agent are generally applied using a suitable delivery device or system. Such a device is, e.g., an applicator that serves to jet, spray or drip the two separate liquids on the teeth and, particularly, between the teeth. The gelable liquid is applied via an aperture configured to exit the gelable liquid into an interdental space. Such an aperture may be a nozzle, such as the dispensing nozzle of an applicator for liquids. The aperture may also be the inside of a dental tray configured to be placed around teeth. The inside hereby refers to the side of the walls of a dental tray configured to face the teeth upon placement of the dental tray over teeth. Such a dental tray can be filled with the gelable liquid manually, such as by squeezing from a tube similar to a tube for toothpaste. A dental tray can also be filled with gelable liquid via an automated dispensing system, through one or more nozzles present in a wall of the dental tray.

Applying the gelling agent into the applied gelable liquid can be accomplished in several ways. It will be understood that thereby an applicator is needed that is suited to apply the gelling agent into the gelable liquid, rather than onto it. One such applicator is an injector, such as a syringe or a jet injector. This method of application can be conducted by subjects applying the gel in their own mouth, but is particularly suited for a clinical setting, e.g., by a dental practitioner. In the event that the gelable liquid is applied via a dental tray, the liquid gelling agent can either be applied through a separate applicator or via the dental tray. In the former case, the applicator can be configured to be used in the presence of the dental tray, the dental tray can be configured so as to allow the use of a separate applicator for the liquid gelling agent, or both. A separate applicator for the liquid gelling agent can also be used after removal of the dental tray. In the event that a dental tray is used for applying the gelable liquid, it is preferred to provide the dental tray itself with one or more nozzles configured to exit the gelling agent into an interdental space.

Preferably, the invention makes use of an applicator that can be more easily used by subjects themselves. Such an applicator can comprise a system of at least two applicators (delivery system), such as one for the gelable liquid, and one for the gelling agent. The applicator can also be a single applicator (delivery device as opposed to delivery system) adapted to apply both the gelable liquid and the gelling agent. Such an applicator can have a single nozzle, through which both the gelable liquid and the gelling agent can be exited subsequently. Preferably, such a single applicator comprises two separate nozzles. One such nozzle will then be configured to apply the gelable liquid, and the other nozzle will be configured to apply the gelling agent.

Thus, in one aspect, the invention is a delivery system for the application into an interdental space of a gelable liquid comprising an oral care agent and a liquid gelling agent for said gelable liquid. Thereby the system comprises a first container holding the gelable liquid, said first container being in fluid communication with a nozzle configured to exit the gelable liquid into an interdental space. The system further comprises a second container holding the liquid gelling agent, said second container being in fluid communication with a nozzle configured to exit the gelling agent into an interdental space. In accordance with the invention, the system is designed such as to prevent the gelling agent and the gelable liquid to come into contact with each other before both have been exited. This serves to prevent too early gelation, which would result in the delivery system becoming clogged with gel already formed within the system, rather than in the mouth. Further, the system is configured to allow the gelable liquid to be exited prior to the gelling agent. This order of events serves to be able to apply the gelling agent into an applied portion of the gelable liquid.

In preferred embodiment of an applicator device, a nozzle to deliver the gelable liquid (i.e., typically a viscous polymer solution) to the interproximal space is present, which is connected to a handle having a container or cartridge with the solution. A pump serves to provide the dose if the user pushes a button starting an electronically operated pump. A manually operated pump can also be used, as the volumes to deposit are relatively small. E.g., a volume in a range of from 40 to 80 microL will generally be sufficient to fill interdental spaces. Preferably a seal is provided around the nozzle, in order to prevent the viscous solution flowing in other directions than through an interproximal space.

Figure 1:
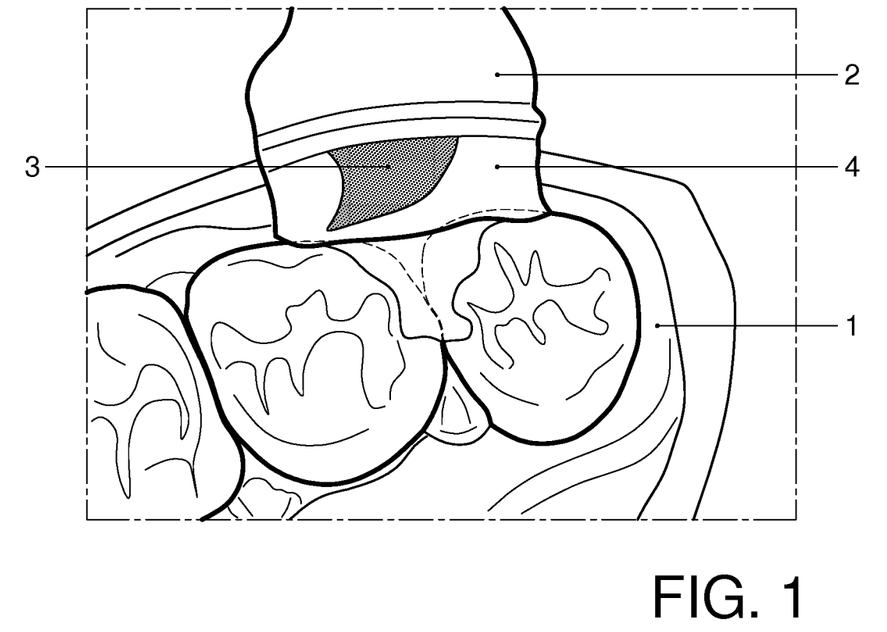
FIG. 1 is a schematic drawing showing a nozzle provided with a seal, in accordance with an embodiment of the invention.

An example of such a seal is shown in FIG. 1. This is a schematic drawing of a model dentition (1) above which a nozzle (2) is held through which a gelable liquid is applied. The gelable liquid is visible as a shaded substance (3) exited from a nozzle opening (not shown). Extending from the nozzle opening, and surrounding the exited liquid, is an annular seal (4).

The nozzle diameter is preferably not too small, and is preferably between 0.3 mm and 3 mm, such as between 0.5 mm and 2 mm, particularly between 1 mm and 1.5 mm. E.g., an AirFloss® nozzle of 1.2 mm diameter works well.

The diameter of the nozzle for applying the liquid gelling agent preferably is between 0.2 and 0.5 mm. A smaller diameter is less preferred, due to the smaller amount of the gelling agent that will be deposited. A larger diameter is less preferred since more care will have to be taken to achieve penetration into the applied gelable liquid, rather than displacement thereof. More preferably, the diameter is 0.3 to 0.4 mm.

It will be understood that the distance to the interproximal space may vary. If necessary, the nozzle can be placed on the teeth, or partially inside the applied gelable liquid. This latter mode of operation serves to reduce the jet velocities for penetration, as the travel distance though the chitosan solution is reduced.

It will also be understood that the position of the nozzle for the liquid gelling agent relative to the nozzle for the gelable liquid is optimally chosen such as to prevent the gelable liquid from becoming subject to gelation at the exit of the nozzle.

A simple solution offers a delivery device for the liquid gelling agent as a separate system. This comprises a separate nozzle and handle, having a fluid path to a container holding the liquid gelling agent (i.e., the cross-linker solution) and a pump in said path to generate the required jet velocity and an activation button as user control. In this embodiment the user may first deposit the polymer solution in all interdental spaces and secondly jet in the cross-linker solution in the spaces using the second system. The polymer solution thereto is preferably on the high viscous end, not to be flowing out and swallowed due to mixing with saliva in the time before the cross-linker is applied. The user may choose to alternate both systems and after each or a few spaces filled with polymer, jet in the cross-linker.

In another embodiment the two nozzles are combined. The advantage thereof, as opposed to separate systems, is that the user does not need to repeat the procedure twice, and that loss of gelable liquid in between applying the two systems is avoided.

It is preferred to prevent the liquid gelling agent (such as a cross-linker solution) from reaching the nozzle exit for the gelable liquid. To this end, a seal is designed that separates the two fluid paths in front of the interdental space, so they can only combine in the interdental space.

Figure 2:
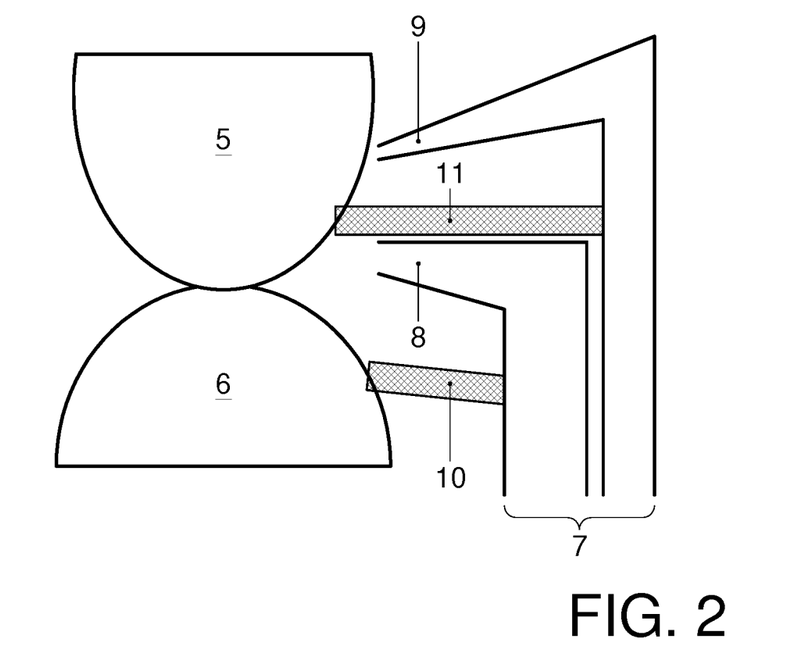
FIG. 2 is a schematic representation of an embodiment of a system of the invention having two nozzles.

This embodiment of the system of the invention is schematically shown in FIG. 2. In this figure a tooth (5) shown adjacent to a gum (6). In proximity with the tooth, a system (7) is held comprising a first nozzle (8) and a second nozzle (9). In this illustration, the first nozzle is intended for the application of a gelable liquid, such as a polymer. The system is provided with a first seal (10) limiting the area to which the gelable liquid can flow at the gum side. The second nozzle, in this illustration, is intended for the application of a liquid gelling agent, such as a crosslinker. A second seal (11) is provided between the exit of the two nozzles, thus separating the area to which the gelling agent can flow from the area to which the gelable liquid can flow.

For this embodiment it is preferred to deliver the jet of the liquid gelling agent in such way as to just fill the gelable liquid deposited in the interdental space, i.e. without substantial spilling of liquid gelling agent in the surroundings. This helps preventing the gelable liquid from getting covered with gelling agent at the nozzle exit.

In another preferred embodiment, which stands out as being user friendly, both the gelable liquid and the liquid gelling agent are applied through a dental tray. The tray will preferably cover the full dentition (upper and lower jaw at the same time or separately), and is preferably provided with jet nozzle holes at the interproximal positions. The tray can be custom made, as is generally known in the art, so as to fit the dentition of a user. The user will be able to fill the tray with gelable liquid, and bite to get the liquid to flow into the interdental spaces. A pump is provided to drive the liquid gelling agent, as jets having the desired velocity, in order to apply same into the gelable liquid present in the interdental spaces.

The invention results in the formation of an interdental gel comprising an oral care agent. Particularly, this refers to a gel when present in one or more interdental (interproximal) spaces of an animal, particularly a human subject. The gel of the invention is defined with reference to it being obtainable by a method for the in situ formation thereof in said one or more interdental spaces. The method thereby comprises first applying a gelable liquid comprising the oral care agent into an interdental space, and subsequently applying a corresponding liquid gelling agent into the gelable liquid. The fact that, according to the invention, the gelling agent is applied into (rather than onto) the gelable liquid discriminates the gel, when formed in an interdental space, from oral care gels known in the art. Thus, e.g., a difference reflected by the described application method is that the gelation (typically: crosslinking): takes place from within the gelable liquid. In other words: from the inside to outside rather than, as would be customary, from the outside to the inside.

In a further aspect, the invention is a method of applying a gel comprising an oral care agent into an interdental space. This aspect also extends to a kit of parts for use in applying a gel comprising an oral care agent into an interdental space. Herein the composition comprises, as a first component, a gelable liquid comprising the oral care agent and, as a second component, a corresponding gelling agent. The gel is obtainable by a method for the in situ formation of said gel in said interdental space, as substantially described above.

Compositions suitable for the in situ formation of an oral care gel are known. Generally, such oral care gels are hydrogels formed from a polymer solution (i.e., a gelable liquid) and a crosslinker solution (i.e., a liquid gelling agent). Both solutions are generally aqueous, i.e., wherein the solvent comprises water or a water-miscible liquid.

Examples of gelable liquids are polymer solutions of chitosan (typically dissolved in a diluted acid such as acetic acid), of sodium alginate (typically dissolved in water), of carrageenan (typically dissolved in water), or of xanthan gum (typically dissolved in water). The corresponding gelling agents for chitosan are, e.g., sodium triphosphate or sodium citrate. The corresponding gelling agent for sodium alginate, carrageenan, and xanthan gum, is an aqueous solution of a calcium salt, preferably calcium chloride.

Other combinations of gelable liquids and corresponding liquid gelling agents are known to the skilled person. The invention provides a technical method, independent of the specific chemistry of the gel components, to apply a two-component gelation system in such a way as to allow gel-formation to occur in an interdental space.

A preferred system comprises an acidic solution of chitosan as the gelable liquid, and an aqueous solution of sodium triphosphate or citric acid as the liquid gelling agent.

Generally, the gelable liquid will have a viscosity that is sufficiently low for the liquid to be applied into an interdental space, yet sufficiently high for the applied liquid to be held in said space prior to being subjected to gel-formation. In the event that the viscosity is relatively low, the skilled person will know to apply, to the extent necessary, a higher amount of the gelable liquid in order to compensate for amounts of the gelable liquid that may become washed-away by saliva before the gelable liquid is subjected to gel-formation. Also, the skilled person will understand that the less viscous (and/or thinner) the applied gelable liquid is, the less time one should desirably allow to pass until applying the corresponding gelling agent. In general, the gelable liquid will have a viscosity (dynamic viscosity) in a range of from 1 Pa s to 200 Pa s, preferably of from 5 Pa s to 100 Pa s, more preferably of from 20 Pa s to 50 Pa s.

In order to apply the liquid gelling agent into the applied gelable liquid, it is recommended to take into account the velocity (injection speed or jet speed) by which this is done. Particularly, it is recommended to take into account said velocity relative to the viscosity of the applied gelable liquid. By way of general guidance, a lower viscosity of the gelable liquid will be desirable combined with a relatively low velocity of applying the liquid gelling agent, to provide a better result. As the skilled person will understand, a gelable liquid of relatively low viscosity will be better penetrated by a liquid gelling agent jetted into it at a relatively low speed. At a relatively high speed, a low viscosity gelable liquid would be more prone to being displaced, rather than penetrated, by the force of a liquid jetted into it. The opposite holds for a gelable liquid of relatively high viscosity. In such a case, a low velocity jet of a gelable liquid would possibly not lead to an optimal penetration of the gelable liquid sufficiently deeply to bring about a desired degree of gelation. In such event, a relatively high jet velocity is desired for the liquid gelling agent so as to bring about a desirable degree of gelation. The jet velocity can further be related to the diameter of such jet. Generally, a smaller diameter will allow a higher speed, whilst a larger diameter will enable a lower speed. This too can be understood in relation to the desire to penetrate, rather than displace, the applied gelable liquid with a fluid jet of the liquid gelling agent. E.g., at a viscosity of the applied gelable liquid of 100 Pa s, the jet speed of the liquid gelling agent can be, e.g., 15 m/s in the event of a relatively small jet diameter (e.g. a diameter of 0.2 mm).

The skilled person will be able to choose the appropriate combinations of viscosity of the gelable liquid and jet velocity of the liquid gelling agent without undue difficulty. Yet, further guidance can be obtained from the schedule given in Table 1 below. Thereby the jet diameter will generally be equal to the corresponding nozzle diameter. In table 1, in the first column, various ranges of viscosities are given for the gelable liquid. The second and third column provide suggested ranges for the corresponding jet velocities, at two different nozzle diameters. These jet velocities refer to the speeds at which, at viscosities within said ranges, liquid gelling agent is exited and sent into an applied gelable liquid (i.e., ranges for the jet speeds for applying the liquid gelling agent).

TABLE 1

Jet speed guidance for the application of liquid gelling agent

| | Jet diameter (mm) | |
| --- | --- | --- |
| Viscosity of gelable liquid | 0.2 mm | 0.5 mm |
| 3-5 Pa s | 5-8 m/s | 3-5 m/s |
| 30-40 Pa s | 8-11 m/s | 6-8 m/s |
| 80-100 Pa s | 10-15 m/s | 8-10 m/s |

A desirable viscosity of the gelable liquid, such as a chitosan solution, to retain it long enough during application and crosslinking in the interproximal space may go as low as 1 Pa s, at which penetration velocities down to 2 m/s for a 0.5 mm jet are sufficient. However, for the strength of the resulting gel it is preferred to have high viscosity solutions, e.g. 25 Pa s to 100 Pa s.

As for the jet timing it is preferred for a better mixing of the cross-linker in the liquid gelling agent with the chitosan solution to have a short jet timing with a slightly higher velocity than a longer time with a lower velocity. Without wishing to be bound by theory, the inventors believe that a higher velocity causes a somewhat larger extent of turbulence and mixing. An additional advantage of short timing is the lower volume of cross-linker solution used. E.g., using the 0.5 mm nozzle, a 20 ms shot at 4.8 m/s produces 19 microL, while a 60 ms shot at 4.2 m/s uses 49 microL.

In another preferred embodiment the jet is used at different velocities, an initial high velocity to ensure full penetration of the polymer solution in the interdental space and a later low velocity covering the front of the solution. This method involves, e.g., using a fast 10 ms shot and a subsequent 10 ms lower velocity shot, and results in an optimally complete gel formation. In this embodiment it is also conceivable to apply a single shot, yet allow this to start at a high velocity and then reduce the velocity over time.

In a preferred embodiment, the gelable liquid is based on chitosan.

Preferred ranges for jet speeds in the event of an acidic chitosan solution as a gelable liquid and an aqueous solution of sodium triphosphate as a as liquid gelling agent are given in Table 2.

TABLE 2

Jet speed guidance for the application of liquid gelling agent

| | Jet diameter (mm) | |
|---|---|---|
| Viscosity of gelable liquid | 0.2 mm | 0.5 mm |
| 5 Pa s | 5.5-6.8 m/s | 4.2-4.8 m/s |
| 30 Pa s | 8.6-9.3 m/s | 6.2-6.8 m/s |
| 100 Pa s | 14-15 m/s | 9-10 m/s |

Chitosan is produced commercially by deacetylation of chitin, which is the structural element in the exoskeleton of crustaceans (such as crabs and shrimp) and cell walls of fungi. On average, the molecular weight of commercially produced chitosan is between 3800 and 20,000 Daltons. A common method for the synthesis of chitosan is the deacetylation of chitin using sodium hydroxide in excess as a reagent and water as a solvent. Chitosan has the following structural formula (formula 1):

(1)

In practice deacetylation is not 100%, and generally more than 60%, leaving a number of aminoacetyl groups at the amine position. Thus, chitosan has NH2 groups, which can be partially protonated (NH3+), depending on the pH. At neutral pH (7) and acidic pH the net charge of chitosan is positive, having a relatively low adhesive (even locally repelling) electrostatic interaction with positively charged antimicrobial agents, such as CPC, chlorhexidine or metal ions (Zn2+, Sn2+, Ag+, Cu2+).

In accordance with the invention, chitosan can also be a derivatised chitosan, such as methylated chitosan in which some or all of the amino groups are methylated, such as trimethylated chitosan.

In making the in situ hydrogel formulations of the invention, chitosan is provided in the form of an aqueous solution. Generally, such a solution will comprise of from 0.5 wt. % to 5 wt. % of chitosan, preferably 1-3 wt. %, such as 1-2 wt. %. As the skilled person will be aware, the concentration of chitosan can depend on the molecular weight of chitosan. Typically, chitosan is produced in molecular weights ranging from 3800 to 20,000 Daltons. It will be understood that, generally, lower molecular weight chitosan will suitably be provided in higher concentrations, such as the high end of the aforementioned range. Higher molecular weight chitosan will be provided in lower concentrations, such as the low end of the aforementioned range.

The hydrogel formulation of the invention comprises a positively charged antimicrobial agent as the oral care agent. Such agents are well-known to the skilled person. Typical examples include: cetylpyridinium chloride (CPC), chlorhexidine, and agents containing metal ions (Zn2+, Sn2+, Ag+, Cu2+), such as zinc acetate. Suitable antimicrobial (antibacterial) agents include, for example, antimicrobial peptides and sources of certain metal ions such as zinc, copper, silver and stannous ions, for example in salt form such as zinc, copper and stannous chloride, and silver nitrate. These are present in art-known small quantities when used. Typical oral care agents in common usage are bisguanidines such as chlorhexidine (including chlorhexidine digluconate), cetylpyridinium chloride, stannous fluoride, sodium fluoride, hydrogen peroxide, zinc citrate, benzethonium chloride, zinc lactate, herbal extracts (e.g. sanguinarine). Preferred agents for use in the invention are CPC and chlorhexidine. The antimicrobial agents are present in concentrations customary in the art. Typical concentrations for CPC or chlorhexidine range from 0.01 to 2 wt. %, preferably 0.05 to 0.5 wt. %, and more preferably of from 0.8 to 0.2 wt. %. For use in mouth rinses, the concentrations will generally not exceed 0.2 wt. % or even 0.12 wt. %.

In making the hydrogel formulations of the invention, the antimicrobial agent can be included in either or both of the chitosan solution and the crosslinker solution (i.e., the liquid gelling agent). It is preferred, however, to include the antimicrobial agent at least in the chitosan solution. It is also conceivable to first mix the solution, and then add the antimicrobial agent. In the latter case, it is advisable to add the antimicrobial agent prior to the conclusion of the cross-linking process of chitosan resulting from the addition of the crosslinking solution.

The liquid gelling agent for chitosan preferably comprises a crosslinking agent selected from the group consisting of tribasic salts, tetrabasic salts, and mixtures thereof. This refers to salts of tribasic or tetrabasic acids. The tribasic or tetrabasic acid can be an acid that has, but for the salt formation, would have three or four acidic groups. The tribasic or tetrabasic acid, however, can also refer to an acid that, but for the salt formation, is based on an acid having a higher number of acidic groups, wherein the number of acidic groups exceeding three or four is in a protonated state. This refers, e.g., to sodium triphosphate (TTP) which is based on triphosphoric acid, which has five acidic groups, and which thus has five alkaline, negatively charged groups. This phosphate can be provided a sodium triphosphate pentabasic, which has five negatively charged groups. In a mono-protonated state, however, the resulting salt is tetrabasic, as it has four remaining negatively charged groups (the fifth group being protonated).

Acidic groups hereby refer to Brønsted acids, i.e. according to which acids are recognized as being proton donors. It is conceivable in the invention to make use, as a crosslinker for chitosan, of a polybasic acid having a higher number of acidic groups than the three or four acidic groups preferred in accordance with the invention. In that event, an additional measure in accordance with the invention is to adjust the pH to such a value as to ensure that the polybasic acid is in the form of a tri- or tetrabasic salt.

Preferred crosslinking agents, as used in the invention, that are based on a polybasic acid of a higher order than required, are triphosphate (TPP) salts, such as sodium triphosphate. TPP can be identified with reference to structural formula (2) below.

(2)

In the invention, an acid such as hydrochloric acid is preferably added to the crosslinker solution that comprises sodium triphosphate, so as to adjust the pH to a value of from 5.5 to 7.5, preferably 6-7. At such a pH, the sodium triphosphate is in a mono-protonated form, and it thus effectively is a tetrabasic acid.

The pH adjustment is suitable conducted in the aqueous crosslinker solution. By virtue of the strong buffer capacity of TPP, the pH resulting from combining the crosslinker solution and the chitosan solution will generally have the same value as that of the crosslinker solution. This is all the more secured in the event that, as preferred, the amount of the crosslinker solution used is higher than that of the chitosan solution.

In fact, as a general preference in the present invention, the weight ratio of the crosslinker solution to the chitosan solution, taking the amounts in which both solutions are administered, ranges of from 0.5:1 to 5:1, such as of from 1:1 to 3:1. Hereby it is noted that a further excess of the crosslinker solution is can be well-tolerated, as such will generally be naturally washed away by saliva upon administration to the oral cavity. It is further noted that the ratio as present in an interdental space, after administration according to the invention, preferably may ranges from below 1:1, such as from 0.25:1, such as from 0.5:1, to 2:1 or lower, such as up to 1.5:1, such as up to 1:1. It is preferred to have in majority chitosan in an interdental space.

Thus, in an interesting embodiment, the crosslinking agent is sodium triphosphate, and as an additional measure a sufficient amount of an acid is added to the crosslinker solution to set the pH of said solution to a value of from 5.5 to 7.5, preferably 6-7. Suitable acids are, e.g., strong inorganic acids, such a nitric acid, sulfuric acid, or hydrochloric acid. Additionally weaker organic acids such as lactic acid, citric acid or acetic acid could be used to adjust the pH.

It is also conceivable to use a crosslinking agent that does not require a pH adjustment in order to provide the desired number of negatively charged groups. A preferred example of such a crosslinking agent is sodium citrate. This is a tribasic salt not requiring a pH adjustment. Thus, in an interesting embodiment, a citrate salt is used as a crosslinking agent for chitosan comprising a positively charged antimicrobial agent. This serves to provide, beneficially without a pH adjustment step, to provide a chitosan hydrogel comprising a positively charged antimicrobial agent and at least one free negatively charged group per molecule of crosslinking agent in the hydrogel.

It is preferred according to the invention to employ a crosslinking agent having four negatively charged groups. Thus, the tetrabasic salts are preferred as crosslinking agents. In a further preference, this tetrabasic salt is a triphosphate salt at pH 5.5-7.5, preferably at pH 6-7. More preferably this is realized by means of the judicious addition of an acid.

The salts used as crosslinking agents in the invention can be based on a wide range of cations. Typical cations are alkali metal ions, such as sodium or potassium, earth alkali metal ions, such as calcium or magnesium, and ammonium ion. Sodium ions are generally preferred.

Establishing an effective, chitosan-gelling amount of the crosslinking agent as such does not present a difficulty to the skilled person. The concentration of the salt in the chitosan hydrogel will generally be of from 30 mM to 300 mM, such as of from 50 mM to 250 mM, such as of from 70 mM to 233 mM end concentration in gel. Higher amounts will technically be possible, though not technically necessary and more costly. Lower amounts than, typically, 25 mM may tend to reduce the number of bound negatively charged groups in the gel, which will reduce the strength of the gel and the speed of crosslinking.

In an interesting embodiment, the system of the invention is adapted so as to provide a longer residence time. To this end, the solutions can be so formulated as to have an increased viscosity, e.g., by adding thickeners, such as carrageenan or poloxamers.

The in situ interdental gel provided in accordance with the invention is not only suitable to combat dental plaque, but preferably also for the purpose of inhibiting or preventing regrowth of dental plaque. Such inhibition or prevention of regrowth thereby preferably pertains to circumstances wherein, prior to application of the system of the invention, dental plaque has been removed by a plaque removing oral care treatment such as brushing of teeth and/or gums, oral rinsing, oral irrigation, or a combination of these and/or other plaque-removing treatments. The application of the system according to the invention then serves to provide antimicrobial agents, in a sustained manner, thereby preventing, or at least inhibiting regrowth. Inhibiting can refer to, e.g., delaying regrowth, or to resulting in a regrowth of a lower amount of bacteria.

In accordance herewith, the invention also provides a method for the treatment or prevention of dental plaque in a subject, particularly a human subject. The method makes use of a gelable liquid comprising at least one anti-plaque agent, such as an antimicrobial agent, and a liquid gelling agent for the gelable liquid, particularly presented in the form of a system as substantially described hereinbefore. The method comprises first applying the gelable liquid into an interdental space of the subject, applying the gelling agent into the applied gelable liquid, and allowing the gelable liquid and the gelling agent to form a gel in said interdental space. In a related aspect, the invention presents the system as substantially described hereinbefore, for use in said method for the treatment or prevention of dental plaque.

Apart from, or in addition to, the administration of an antimicrobial agent, the system of the invention, as described hereinabove, can also be used for the administration of a plurality of different agents. Thus, the system of the present invention can also serve as a carrier to administer one or more oral care agents other than antimicrobial agents to the teeth and/or gums.

Such additional oral care agents are preferably selected from the group consisting of anti-inflammatory agents, antiplaque agents, anti-tartar agents, anti-gingivitis agents, anti-bacterial agents, anti-caries agents, anti-sensitivity agents, and combinations thereof.

A preferred anti-caries agent is fluoride. Suitable fluoride sources include sodium fluoride, stannous fluoride, sodium monofluorophosphate, zinc ammonium fluoride, tin ammonium fluoride, calcium fluoride, cobalt ammonium fluoride potassium fluoride, lithium fluoride, ammonium fluoride, zinc ammonium fluoride, tin ammonium fluoride, calcium fluoride, cobalt ammonium fluoride, water soluble amine hydrofluorides, or mixtures thereof. The fluoride is preferably present in an amount of at least 0.001%, more preferably, from 0.01 to 12%, and most preferably, from 0.1 to 5% by weight of the total liquid applied into the oral cavity.

The invention will further be illustrated with reference to the following non-limiting example and the accompanying figures.

EXAMPLE

Figure 3:
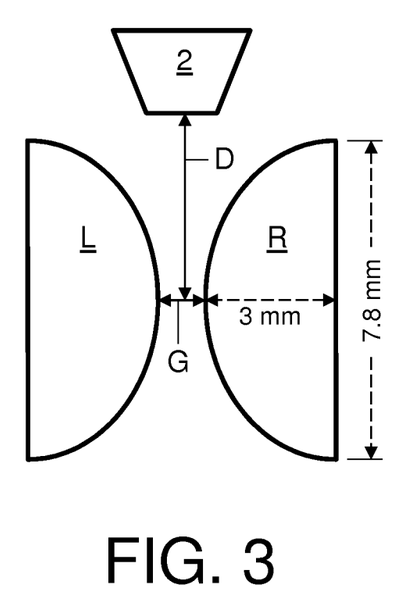
FIG. 3 is a schematic drawing of a model interproximal space as used in the Example.

In this example a test is conducted to optimize jet velocities so as to fully penetrate an interdental space filled with viscous polymer solution. To this end a transparent model space was made. This model space is schematically illustrated in FIG. 3. Tests were performed to identify the threshold velocity for complete cross-linker jet penetration.

Figure 4:
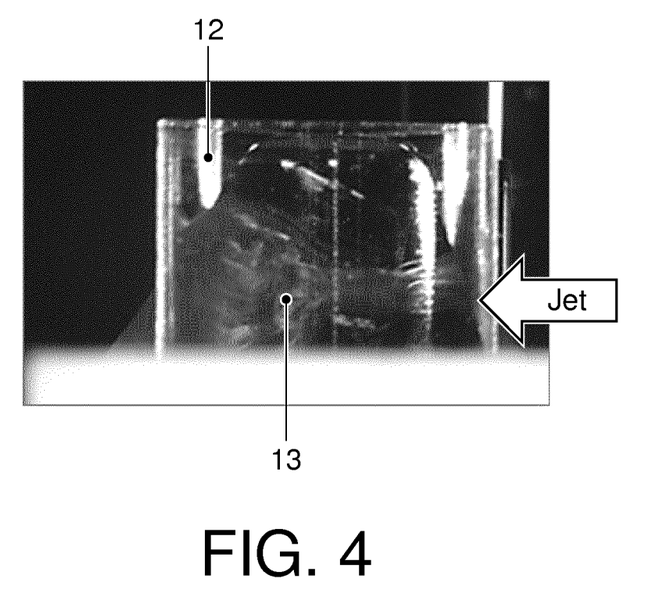
FIG. 4 is a photograph of a chitosan solution into which a gelling agent has been applied in accordance with the invention, and as described in the Example.

The model comprises two transparent half circles L and R (height 4 mm) that together form a model interproximal space having a gap width G of 0.4 mm. The space was filled with chitosan solution, and a jet of cross-linker solution was ejected as a jet D from the nozzle. Images from the viewpoint of the eye were taken after the mixing to assess the penetration depth of the jet. This refers to the photograph in FIG. 4. In this photograph, the model is visible with reference to a transparent confinement (12) within which a gelable liquid is held (not visible if not gelled). Into said confinement a liquid gelling agent is jetted (the direction indicated by an arrow). Cross-linked gel is visible as an opaque substance (13).

The results for the optimized jet speeds are laid down in Table 2 above. The optimal viscosity of the chitosan solution to retain it long enough during application and crosslinking in the interproximal space may go as low as 1 Pa s, at which penetration velocities down to 2 m/s for a 0.5 mm jet may be sufficient. For strength of the resulting gel it is more preferred to have high viscosity solutions, e.g. 25 to even 100 Pa s. At 100 Pa s the jet speed may need to be 15 m/s if the jet has a small (e.g. 0.2 mm) diameter.

As for the jet timing a further optimization for mixing the cross-linker with the chitosan solution appears to have a short jet timing with a slightly higher velocity, rather than a longer time with a lower velocity. With higher velocities, more care needs to be taken in view of the potential occurrence of turbulence and mixing. An additional advantage of short timing is the lower volume of cross-linker solution used. Using the 0.5 mm nozzle, a 20 ms shot at 4.8 m/s produces 19 microL, while the 60 ms shot at 4.2 m/s uses 49 microL.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein two different antimicrobial agents are used, preferably one in either solution.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum, we hereby disclose a method, and a system, for accomplishing the in situ formation of a gel in an interdental space. This is useful for the interdental application of one or more dental care agents, such as antimicrobial agents or other anti-plaque agents. The invention makes use of a two component system comprising a gelable liquid and a liquid gelling agent capable of bringing about gelation of the liquid. Typically, the gelable liquid is a polymer or a polymer solution, whereby the liquid gelling agent is typically a crosslinker. A suitable system is, e.g., that of an aqueous chitosan solution as the gelable liquid, and an aqueous solution of a crosslinking agent (e.g. a tribasic or tetrabasic salt, such as sodium triphosphate) or, or, e.g., citric acid. The system of the invention is arranged such that first the gelable, typically viscous, liquid can be applied, and then the liquid gelling agent is forced, e.g. jetted, into the applied gelable liquid. The system is designed such as to prevent the gelling agent and the gelable liquid to come into contact with each other before both have been applied. The system is configured to allow the gelable liquid to be applied prior to the gelling agent.

The invention claimed is:

1. A delivery system for the application into an interdental space of a gelable liquid and a liquid gelling agent, at least one of the gelable liquid and the liquid gelling agent comprising an oral care agent,
wherein the delivery system comprises:
a first container for holding the gelable liquid;
an aperture configured to exit the gelable liquid into an interdental space, the container being in fluid communication with the aperture;
a second container for holding the liquid gelling agent;
a nozzle configured to exit the gelling agent into the interdental space, the second container being in fluid communication with the nozzle,
the nozzle and the aperture being configured to allow the gelable liquid to exit the aperture prior to allowing the liquid gelling agent to exit the nozzle; and
a seal in proximity to the aperture and in a position where it is capable of preventing gelable liquid from flowing in a direction toward the nozzle.

2. A system according to claim 1, wherein the system comprises a single applicator comprising the nozzle and a separate further nozzle comprising the aperture, and wherein the seal lies between the nozzle and the separate further nozzle.

3. A system according to claim 1, wherein the aperture is second nozzle, and wherein the seal is in an annular seal around the second nozzle.

4. A system according to claim 1, wherein the aperture is a nozzle having a diameter between 0.3 mm and 3 mm.

5. A system according to claim 1, wherein the diameter of the nozzle is between 0.2 and 0.5 mm.

6. A system according to claim 1, wherein the diameter of the nozzle is between 0.3 mm and 0.4 mm.

7. A system according to claim 1, wherein the aperture is a nozzle having a diameter between 0.5 mm and 2 mm.

* * * * *